United States Patent [19]

Teutsch et al.

[11] 4,353,899
[45] Oct. 12, 1982

[54] NOVEL 16α-METHYL-PREGNANE

[75] Inventors: Jean G. Teutsch, Pantin; Roger Deraedt, Pavillons-sous-Bois, both of France

[73] Assignee: Roussel Uclaf, Paris, France

[21] Appl. No.: 300,252

[22] Filed: Sep. 8, 1981

Related U.S. Application Data

[63] Continuation of Ser. No. 170,627, Jul. 21, 1980, abandoned.

[30] Foreign Application Priority Data

Jul. 26, 1979 [FR] France .................. 79 19296

[51] Int. Cl.$^3$ .................................. A61K 31/56
[52] U.S. Cl. ........................ 424/243; 260/397.45
[58] Field of Search ............... 424/243; 260/397.45

[56] References Cited

FOREIGN PATENT DOCUMENTS 2342738 10/1968 France .................. 260/397.45
1068099  5/1967 United Kingdom ...... 260/397.45

*Primary Examiner*—Elbert L. Roberts
*Attorney, Agent, or Firm*—Hammond & Littell, Weissenberger and Muserlian

[57] ABSTRACT

The novel product, 9α,11β-dichloro-16α-methyl-21-oxycarbonyldicyclohexylmethoxy-Δ$^{1,4}$-pregnadiene-3,20-dione, having surprenant "in loco" anti-inflammatory activity without any systemic anti-inflammatory activity and its preparation.

4 Claims, No Drawings

NOVEL 16α-METHYL-PREGNANE

This is a continuation of Ser. No. 170,627 filed July 21, 1980 now abandoned.

STATE OF THE ART

French Pat. No. 2,342,738 describes compounds of the formula

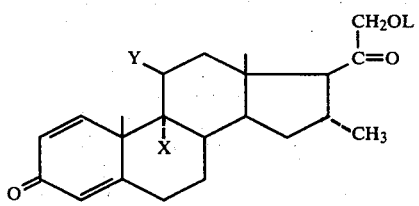

wherein L is selected from the group consisting of hydrogen and acyl of an organic carboxylic acid of 1 to 18 carbon atoms, Y is a 11β-chloro and X is 9α-chloro or bromo or Y is a 11β-fluoro and X is a 9α-chloro. French patent of addition No. 2,381,065 describes and claims 9α,11β-dichloro-16α-methyl-Δ$^{1,4}$-pregnadiene-21-ol-3,20-dione. Both describe the compounds as having general anti-inflammatory activity, especially 9α,11β-dichloro-16α-methyl-21-acetoxy-Δ$^{1,4}$-pregnadiene-3,20-dione.

OBJECTS OF THE INVENTION

It is an object of the invention to provide the novel product, 9α,11β-dichloro-16α-methyl-21-oxycarbonyldicyclohexylmethoxy-Δ$^{1,4}$-pregnadiene-3,20-dione and a process for its preparation.

It is another object of the invention to provide novel "in loco" anti-inflammatory compositions and to provide a novel method of combatting inflammation "in loco" in warm-blooded animals.

These and other objects and advantages of the invention will become obvious from the following detailed description.

THE INVENTION

The novel product of the invention is 9α,11β-dichloro-16α-methyl-21-oxycarbonyldicyclohexylmethoxy-Δ$^{1,4}$-pregnadiene-3,20-dione.

The process of the invention for the preparation of the said novel product comprises reacting 9α,11β-dichloro-16α-methyl-Δ$^{1,4}$-pregnadiene-21-ol-3,20-dione with a compound of the formula

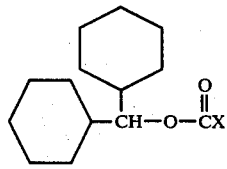

A wherein X is a halogen to obtain the desired compound. X is preferably bromine or chlorine. Compound A is preferably the chloroformate of dicyclohexylcarbinol and the reaction is effected in the presence of a basic agent such as pyridine or collidine.

The novel "in loco" anti-inflammatory compositions of the invention are comprised of an anti-inflammatorily effective amount of 9α,11β-dichloro-16α-methyl-21-oxycarbonyldicyclohexylmethoxy-Δ$^{1,4}$-pregnadiene-3,20-dione and an inert pharmaceutical carrier or excipient. The compositions may be in the form of powders, pomades, cremes, gels or aerosol preparations.

Examples of suitable excipients are aqueous or non-aqueous vehicles, fatty bodies of animal or vegetable origin, paraffinic derivatives, alcohols such as glycols, diverse wettings agents, dispersants or emulsifiers, preservatives, talc, and starch.

The compositions of the invention have only an "in loco" activity as compared to the prior art compounds which have a general anti-inflammatory activity and are not active orally. This disassociation of "in loco" activity vs general anti-inflammatory activity is useful as the compositions may be used without worry of the classical side effects of the cortisone type. This disassociation of activity is particularly interesting for aerosol preparation.

The compositions of the invention are useful for the treatment of asthma as well as edemas, dermatosis, pruritus, diverse forms of eczema and solar erythema.

The novel method of treating "in loco" inflammation in warm-blooded animals, including humans, comprises administering, "in loco" an anti-inflammatorily effective amount of 9α,11β-dichloro-16α-methyl-21-oxycarbonyldicyclohexylmethoxy-Δ$^{1,4}$-pregnadiene-3,20-dione. The said compound is applied to the skin or mucous. The dose will vary depending on the individual treated and the specific cause of inflammation but a useful aerosol dose is 1 to 6 sprays per day of an aerosol preparation to administer 0.1 to 2 mg of the product per spraying.

In the following example there are described several preferred embodiments to illustrate the invention. However, it is to be understood that the invention is not intended to be limited to the specific embodiments.

EXAMPLE

9α,11β-dichloro-16α-methyl-21-oxycarbonyldicyclohexylmethoxy-Δ$^{1,4}$-pregnadiene-3,20-dione A solution of 2 g of 9α,11β-dichloro-16α-methyl-Δ$^{1,4}$-pregnadiene-21-ol-3,20-dione (prepared in French patent of addition No. 2,381,065) in 4 ml of pyridine and 8 ml of dioxane was cooled to 0° to 5° C. and a solution of 4 ml of the chloroformate of dicyclohexylcarbinol in 12 ml of dioxane was added thereto. The temperature was allowed to rise to 20°–25° C. and the mixture was stirred for 5 hours and was poured into ice water. The mixture was extracted with chloroform and the organic phase was washed with 0.1 N sulfuric acid and then with water and evaporated to dryness to obtain a residue of 5.9 g. The residue was chromographed over silica gel and was eluted with a 1-1 ether-petroleum ether (b.p.=60° to 80° C.) mixture and then with a 3-1 ether-petroleum ether mixture to obtain 3.288 g of a resin with an Rf=0.16. The resin was dissolved in hot ethanol and the solution was cooled to effect crystallization. The mixture was vacuum filtered and the recovered product was washed with ethanol and dried to obtain 2.8 g of 9α,11β-dichloro-16α-methyl-21-oxycarbonyldicyclohexylmethoxy-Δ$^{1,4}$-pregnadiene-3,20-dione melting at about 140° C. and having a specific rotation of $[\alpha]_D^{20} = +133° \pm 2°$ (c=1% in ethanol).

PHARMACOLOGICAL DATA

The anti-inflammatory activity was determined from the product of the above example [product A], 9α,11β- dichloro-16α-methyl-21-acetoxy-Δ$^{1,4}$-pregnadiene-3,20-dione [product B], dexamethasone and 9α,11β-dichloro-16α-methyl-21-pentanoyloxy-Δ$^{1,4}$-pregadiene-3,20-dione [product C].

A. Oral Anti-inflammatory Activity

The test used was the classical granuloma test which was a modification of the method of Meier et al [Experientia, Vol. 6 (1950), p. 469] using conventional female Wistar rats weighing 100 to 110 g. The rats received an implantation of 2 cotton pellets weighing 10 mg each in the skin of the thorax and the rats then received orally twice a day for 2 days the test products and 16 hours after the last ingestion on the third day, the animals were killed. The pellets together with the granuloma tissue formed was weighed in the fresh state and after 18 hours at 60° C. The granuloma weight was determined by deducting the original cotton weight. The weight of the thymus which was removed at the same time as the granuloma indicated the thymolytic activity of the test compounds. The results expressed in DA$_{50}$ (dose which inhibited the granuloma by 50% and dose which caused a 50% involution of the thymus) are reported in Table I.

TABLE I

| Test Product | DA$_{50}$ Granuloma in mg/kg | DA$_{50}$ Thymus in mg/kg |
| --- | --- | --- |
| A | inactive at 50 | inactive at 50 |
| B | >100 | 50 |
| C | >50 | 15 |
| dexamethasone | 0.050 | 0.035 |

The results of Table I show that product A was inactive at the tested dose while products B and C are only slightly active orally as compared to dexamethasone.

B. "In Loco" Anti-inflammatory Activity

The test procedure is a modification of the above procedure with the rats receiving an implantation of 2 cotton pellets containing the test product under the thorax skin. The pellets were prepared by dissolving the test compounds in 20 μl of ethanol which was placed on each cotton pellet and the pellets were dried at 40° C. for 24 hours and then were implanted. The animals were killed on the morning of the 3rd day and the pellets together with the granuloma tissue were weighed fresh and after 18 hours at 60° C. and the weight of granuloma was determined by subtracting the original cotton weight. The thymus was also removed and weighed to determine the systemic thymolytic activity of the products. The DA$_{50}$ as determined previously is reported in Table II.

TABLE II

| Test Product | DA$_{50}$ Granuloma in mg | DA$_{50}$ Thymus in mg |
| --- | --- | --- |
| A | 0.0008 | inactive at 0.100 |
| B | 0.012 | 0.360 |
| C | >0.100 | >0.100 |
| dexamethasone | 0.400 | 0.025 |

The results of Table II show that product A has a very superior "in loco" anti-inflammatory activity as compared to products B and C and dexamethasone as can be seen from the granuloma test and that products A, B and C have a much lower systemic activity than dexamethasone as can be seen from the thymus test.

EXAMPLE 2

An aerosol was prepared delivering for each dose, 0.5 mg of product A, 0.15 mg of an emulsifier and 50 mg of propellent.

Various modifications of the compositions and method of the invention may be made without departing from the spirit or scope thereof and it should be understood that the invention is to be limited only as defined in the appended claims.

What is claimed is:

1. 9α,11β-dichloro-16α-methyl-21-oxycarbonyldicyclohexylmethoxy-Δ$^{1,4}$-pregnadiene-3,20-dione.

2. An "in loco" anti-inflammatory composition comprising an anti-inflammatorily effective amount of the compound of claim 1 and an inert pharmaceutical carrier.

3. A method of treating "in loco" inflammation in warm-blooded animals comprising applying "in loco" to warm-blooded animals an anti-inflammatorily effective amount of the compound of claim 1.

4. A method of treating asthma in warm blooded animals comprising applying "in loco" to warm blooded animals an anti inflammatorily effective amount of the compound of claim 1.

* * * * *